United States Patent [19]
Folkman

[11] Patent Number: 5,227,372
[45] Date of Patent: Jul. 13, 1993

[54] METHOD FOR RETAINING OPHTHALMOLOGICAL AGENTS IN OCULAR TISSUES

[75] Inventor: Judah M. Folkman, Brookline, Mass.

[73] Assignee: Children's Medical Center Corporation, Boston, Mass.

[21] Appl. No.: 489,680

[22] Filed: Mar. 7, 1990

[51] Int. Cl.$^5$ .................. A61K 31/715; A61K 31/56; C08B 37/16

[52] U.S. Cl. .................... 514/58; 536/103; 514/778; 514/912

[58] Field of Search ............ 514/58, 778, 912; 536/103

[56] References Cited

U.S. PATENT DOCUMENTS

| | | | |
|---|---|---|---|
| 2,923,704 | 2/1960 | Berger et al. | 514/58 |
| 3,754,925 | 8/1973 | Kimura et al. | 435/822 |
| 3,822,250 | 7/1974 | Kimura et al. | 536/1.1 |
| 4,454,315 | 6/1984 | Sasaki et al. | 536/115 |
| 4,877,774 | 10/1989 | Pitha et al. | 514/58 |
| 4,877,778 | 10/1989 | Carpenter et al. | 514/58 |
| 4,935,407 | 6/1990 | Luider et al. | 514/58 |
| 5,007,967 | 4/1991 | Ammeraal | 514/58 |
| 5,010,065 | 4/1991 | Skuballa et al. | 514/58 |
| 5,019,562 | 5/1991 | Folkman et al. | 514/58 |

FOREIGN PATENT DOCUMENTS

| | | |
|---|---|---|
| 0244178 | 11/1987 | European Pat. Off. . |
| 0294239 | 12/1988 | European Pat. Off. . |
| 0312208 | 4/1989 | European Pat. Off. . |
| 0325199 | 7/1989 | European Pat. Off. . |
| 50-36422 | 4/1975 | Japan . |
| 55-83798 | 6/1980 | Japan . |
| WO88/07365 | 10/1988 | PCT Int'l Appl. . |
| WO89/06536 | 7/1989 | PCT Int'l Appl. . |
| 1352938 | 5/1974 | United Kingdom . |
| 1443662 | 7/1976 | United Kingdom . |

OTHER PUBLICATIONS

Lee, et al., Survey of Ophthalmology vol. 29, No. 5, pp. 335-348 (Mar.-Apr. 1985).
Folkman, et al., Amer. J. Pathol., 130:393-400 (Feb. 1988).
Shing, et al., Anal. Biochem. 185, 108-111 (1990).
Ebisu, et al., Journal of Bacteriology, Dec. 1975, pp. 1489-1501, vol. 124, No. 3.
Cherniak, et al., Journal of Biological Chemistry, vol. 239, No. 9, pp. 2986-2990.
Andersen, et al., Arch. Pharm. Chem. Sci., Ed. 11:61-66 (1983).
Armstrong, et al., Anal. Chem. 57:234-237 (1985).
Frank, et al., J. Pharm. Sci., vol. 72, No. 10:1215-1217 (1983).
Folkman, et al., Science 243:1490-1493 (Mar., 1989).
Kaji, et al., Int. J. Pharm. 24 (1985) pp. 79-89.

Primary Examiner—Ronald W. Griffin
Attorney, Agent, or Firm—David G. Conlin; David S. Resnick; Gregory D. Williams

[57] ABSTRACT

A method for retaining ophthalmological agents in ocular tissues is provided comprising complexing an ophthalmological drug or reagent with a sulfated glucan sulfate such as cyclodextrin sulfate and contacting the complex so formed with the ocular tissue.

27 Claims, 2 Drawing Sheets

METHOD FOR RETAINING OPHTHALMOLOGICAL AGENTS IN OCULAR TISSUES

This invention was supported under NIH Grant CA45548 and CA37395 and the U.S. Government has certain rights to the invention.

BACKGROUND OF THE INVENTION

In accordance with the present invention, there is provided a method for retaining ophthalmological agents in ocular tissues comprising complexing an ophthalmological drug or reagent with a sulfated glucan sulfate such as cyclodextrin sulfate and contacting the complex so formed with the ocular tissue.

One of the most frequently discussed problems in ocular therapeutics is the delivery of optimal concentrations of ophthalmological agents at the site of action. This problem is due to a number of factors including the distance between where the drug is administered and where it acts, and the physiological processes which reduce drug concentration as it moves from its administration site to its action site. These processes can be grouped into three categories based on anatomical considerations. See Mishima et al, Survey of Ophthalmology Vol.29, No.5 at 335-348 (1985). The first is tear dynamics, conjunctival and scleral absorption. Second is interaction with the cornea. Third is intraocular distribution including aqueous humor turnover. The extent to which such processes are involved in ocular drug bioavailability is often modified by the physical and chemical properties of the drug as well as by the physical properties of the vehicle used in conjunction with the ocular drug or reagent.

Precorneal drug loss, e.g., precorneal fluid dynamics, plays an exceedingly important role in controlling the amount of drug available for corneal absorption. It is principally influenced by the nature of the vehicle applied. Liquid vehicles, which include liposomes, are subjected to drainage into the nasolacrimal apparatus immediately following instillation, a process whose efficiency is highly dependent on the volume, pH, tonicity, and viscosity of the liquid instilled. In addition, the drug would be diluted by tears secreted by the lacrimal glands and may be lost to the tear proteins as a result of binding, thus further reducing the amount of drug available for corneal absorption.

Drug absorption into the conjunctiva is another route of precorneal drug loss. A portion of the drug lost to the conjunctiva may, however, eventually gain entry to the internal eye. While drug loss to precorneal fluid dynamics is primarily a function of the nature of the drug vehicle, corneal drug absorption is principally controlled by the physical and chemical properties of a drug relative to the properties of the cornea. Of the drug properties, lipophilicity and molecular size play a more important role in corneal drug transport.

In recent years, the traditional view of the cornea as a physical barrier to drug transport has been expanded to include its capacity to metabolize certain drugs in transit. Progress in this area is enhanced by ongoing research efforts in unraveling the full complement of enzyme systems participating in corneal drug metabolism. Among the metabolic enzymes that have been identified are the esterases, catechol-0-methyl transferase, monoamine oxidase, arylhydrocarbon hydroxylase, UDP-glucuronyl transferase, acid phosphatase, beta-glucuronidase, and arylsulfatase. Both direct and indirect evidence indicates localization of these enzymes in the corneal epithelium. Interaction of the vast majority of drugs with these corneal enzymes usually results in a reduction of the amount of drug available for interaction with drug receptors within the eye. This event is, therefore, undesirable.

The vehicle in which a drug is housed can influence the rate and extent of topical ocular drug absorption in several ways: (1) by affecting the duration over which the drug remains in the tear chamber; (2) by affecting the rate of drug release; and (3) by the manner in which the vehicle itself interacts with the corneal epithelial surface. These factors, in turn, are affected by the additives such as buffers, polymers, and preservatives in a given vehicle, by the drug concentration in the vehicle, and by the frequency and order of administration of the vehicle.

The vehicles that are currently commercially available include aqueous solutions, suspensions, ointments, and the Ocusert[R]. Those that are potentially useful include gels, erodible and nonerodible inserts, emulsions, microcapsules, and liposomes. To this list may be added a bioadhesive polymeric system, which is under investigation for oral controlled drug delivery but which can be adapted to control the delivery for ophthalmic drugs.

In the category of potentially useful vehicles, the gels and inserts are the more widely studied. Grass et al., found that erodible films made of 20% polyvinyl alcohol and containing pilocarpine amplified the maximum change in miosis and the duration of miosis in the albino rabbit by a factor of 2 and 5 respectively. Using a similar polymeric film, Saettone et al. demonstrated a twofold increase in the ocular bioavailability of pilocarpine over a aqueous solution in albino rabbits. Moreover, these investigators found that complexing pilocarpine with poly(acrylic acid) further enhanced the ocular bioavailability of pilocarpine by another factor of two. Using polyacrylamide and a copolymer of acrylamide, N-vinylpyrrolidone, and ethyl acrylate as a drug delivery matrix, Urtti et al. observed a threefold increase in the ocular bioavailability of pilocarpine in both albino and pigmented rabbits. In all three instances, the enhanced drug effectiveness was attributed to improved contact time of the vehicle with the cornea.

Unlike ointments and inserts, vehicles such as suspensions, emulsions, microcapsules, and liposomes are liquid-like. As such, they are subjected to removal from the conjunctival sac via drainage, resulting in a residence time of 30 minutes or less in the tear pool. This drainage rate is slightly dependent on the physical nature of the vehicle. For instance, suspensions have been found to be retained in the conjunctival sac longer than solutions. It is expected that other dispersed systems such as liposomes, emulsions, and microcapsules would behave similarly. Although these vehicles remain in the conjunctival sac longer than aqueous solutions, they would be therapeutically useful only if they consistently release the drug at an optimal rate, through a combination of such processes a dissolution, diffusion and partitioning. This is because, unlike solutions, the drug in these vehicles is not immediately available for corneal absorption.

To date, the manner in which liquid vehicles interact with the corneal surface has been neither well studied nor exploited for controlling corneal drug absorption. Obviously, vehicles that may have an affinity for the corneal surface, as exemplified by bioadhesive polymers, must overcome the natural tendency of the cornea to rid its surface of foreign substances. Although a judicious selection of emulsifying agents, polymers, and phospholipids, dispersed systems like emulsions, microcapsules, and liposomes may achieve this goal, it is apparent that continuing efforts will be required to prolong ophthalmological drug action by lengthening the time that the drug or reagent is in the eye.

SUMMARY OF THE INVENTION

In accordance with the present invention there is providing methods for retaining an ophthalmological agent in an ocular tissue comprising complexing the ocular agent with a glucan sulfate such as cyclodextrin sulfate. It has been found, for example, that cyclodextrin sulfate, not only penetrates the cornea, but has an affinity for FGF in ocular tissue which allows it to be used as a vehicle for delivering ophthalmological agents to the eye. It has also been found that blood vessels including newly formed blood vessels contain large amounts of FGF which permits introduction of glucan sulfate complexed to ophthalmological agents to the eye via the circulatory system. The use of glucan sulfates to deliver ophthalmological agents to ocular tissues should significantly increase the bioavailability of the agent at its site of action. This should significantly reduce the amount of agent required to compensate for loss of the ocular agent as discussed above. Moreover, concerns about toxicity of certain agents should also be reduced due to the overall reduction in the amount of agent required.

As used herein the term "ophthalmological agent" means any pharmaceutical, drug, salt thereof, alone or together with any pharmaceutical carrier, diluent or the like, and also means any diagnostic agent reagent which can be eliminated to ocular tissues regardless of whether such reagent has any therapeutic affect on the tissue.

As used herein the term "complex" is used in the broadest sense to include ionic binding, covalent binding, hydrogen binding, and other intra- or intermolecular forces whereby one compliment is associated with another.

As used herein the term "ocular tissue" means the its surrounding limbus, the anterior chamber fluid, he iris, the lens, the vitreous, the retina and choroid and the blood vesels which supply these tissues or surround them.

DETAILED DESCRIPTION OF THE INVENTION

Figure 1:
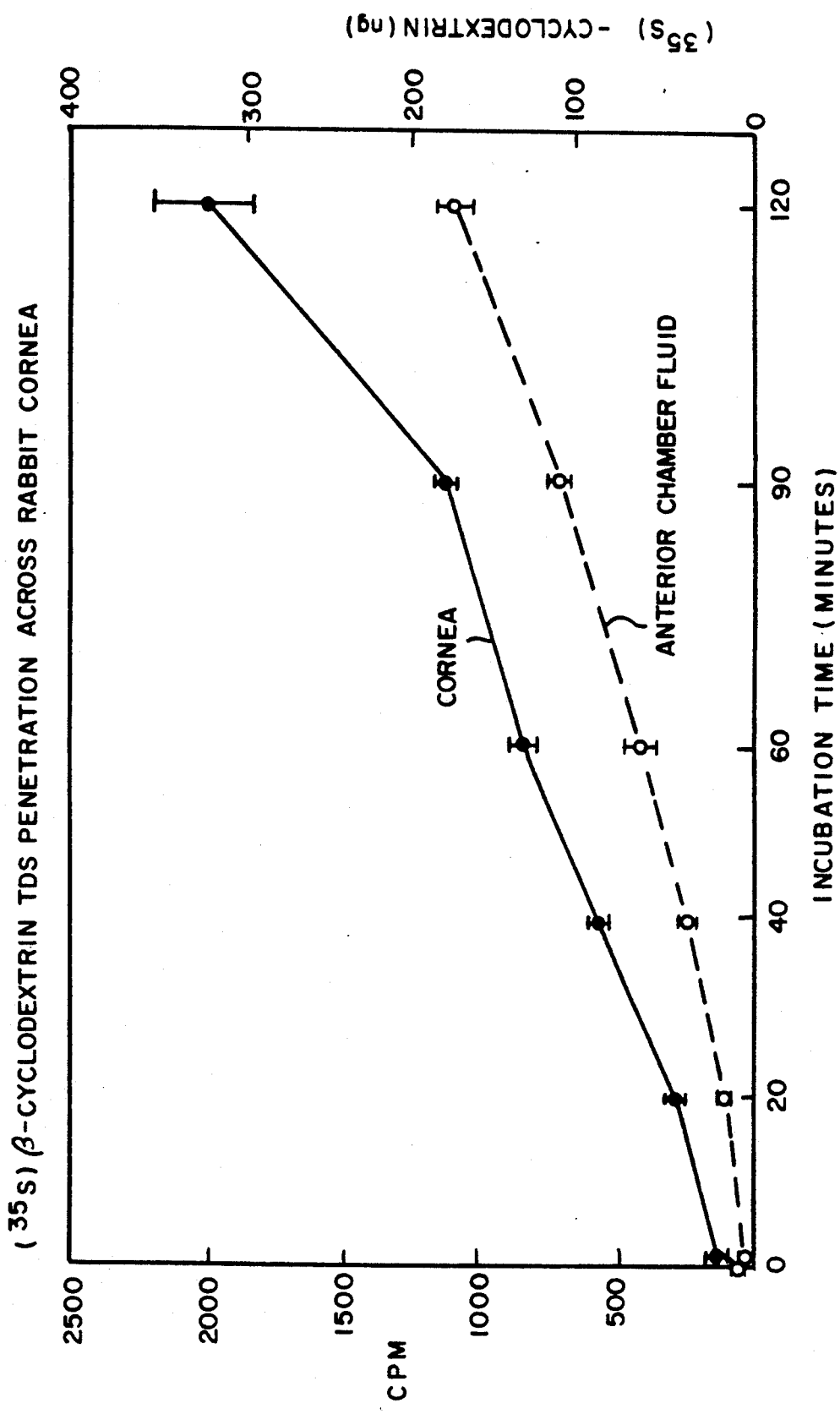
FIG. 1 depicts the penetration of radioactively labelled β-cyclodextrin tetradecasulfate across the rabbit cornea over a period of two hours.

In accordance with the present invention methods are provided for retaining an ophthalmological agent such as a drug or diagnostic reagent at an ocular tissue. In particular the method comprises forming a complex, either prior to administration or in vivo of an ophthalmological agent and a glucan sulfate, and contacting the complex with the ocular tissue.

Certain ocular tissues such as Descemet's membrane and Bowman's membrane are known to contain large amounts of fibroblast growth factor, and in particular basic fibroblast growth factor (FGF). See Folkman et al. Amer. J. Pathol. 130:393–400, (1988). It has also previously been reported that fibroblast growth factor can be purified on a sulfated cyclodextrin column because of the high affinity of FGF for sulfated cyclodextrins such as β-cyclodextrin tetradecasulfate See Shing et al. Anal. Biochem. 185: 1990.

In accordance with one embodiment the present invention it has been found that not only is there corneal penetration of glucan sulfates such as cyclodextrin sulfate, but that such glucan sulfates temporarily bind to and are retained at ocular tissues which contain FGF.

While not wishing to be bound by theory, it is believed that FGF present in certain ocular tissues is acting as "reverse" affinity column which binds glucan sulfate as it diffuses across the cornea. Thus, glucan sulfates such as cyclodextrin sulfate, can be used as a vehicle for transporting and keeping ophthalmological agents in the eye at higher concentrations and for longer periods of time then conventional ocular therapeutic techniques.

In accordance with another embodiment, discussed in more detail below, FGF has been found in the basement membrane of blood vessels (unpublished results), including newly growing blood vessels such as those found in diabetic retinopathy. Thus, in accordance with the present invention glucan sulfates can be used to deliver ophthalmological agents to ocular tissue via the circulatory system. For example, fluroscein can be delivered to the retina and retained there for a period of time longer than in conventional fluorescein angiograms.

Glucan sulfates which can be used in accordance with the present invention include dextran sulfate, cyclodextrin sulfate and β-1,3-glucan sulfate. The preferred glucan sulfate for topical administration is cyclodextrin sulfate as it has been demonstrated that it readily penetrates the cornea. The preferred glucan sulfate for introduction via the circulatory system is also cyclodextrin sulfate although other glucan sulfates discussed below may also be used. Glucan sulfates of the present invention preferably have a sulfur content of not less than 3%(w/w), more preferably between about 12 to 24%(w/w), and most preferably between about 15 to 20%(w/w).

Cyclodextrins are natural cyclic compounds consisting of six (alpha), seven (beta) or eight (gamma) D-glucose units linked by alpha(1→4) linkage. They have a donut-shaped molecular structure which provides a cavity whereby clatherates may form with guest molecules of suitable size. In other words, this internal doughnut-shaped molecule provides a hydrophobic cavity at the center and a hydrophilic outer surface, either of which can be used to carry an ophthalmological agent to the ocular tissues. The diameter of the cavity is determined by the number of glucose units that make up the ring (6, 7, or 8 units for alpha, beta-, or gamma-cyclodextrins respectively.

Cyclodextrin sulfate is an ester resulting from the sulfonation of these cyclodextrins. Sulfonation is achieved by known methods. One preferred method of sulfonation is descried in U.S. Pat. No. 2,923,704 and Japanese Patent Application Laid-open No.36422/1975.

The sulfur content of cyclodextrin sulfate normally exceeds about 3%(w/w), and is preferably between about 12 and 24% (w/w). Such cyclodextrin sulfates are also very soluble in water. Cyclodextrin sulfate containing about 15 to 21% (w/w) sulfur is particularly advantageous.

The alpha, beta, and gamma cyclodextrins sulfate salts are all usable as vehicles for delivery and retaining ophthalmological agents at ocular tissues in accordance with the present invention. $\beta$-cyclodextrin salts such as beta-cyclodextrin tetradecasulfate are preferred.

$\beta$-1,3-glucan sulfate used in the present invention is produced by sulfonating $\beta$-1,3-glucan. $\beta$-1,3-glucan is produced by microorganisms belonging to the genus Alcaligenus or Aorobacterium, has straight chains, is water-soluble and is thermogelable. Processes for purifying various glucans are described in Ebisu et al., Journal of Bacteriology pp.1489–1501, 1975.

Curdlan (also known as thermogelable polysaccharide PS, commercially available from Wako Pure Chemical Industries, Ltd. Japan) is known to be a water-insoluble, thermogelable, unbranched straight chain glucan which has $\beta$-(1->3) linkage alone and which is produce by microbial strains belonging to the genus Alcalioenes or Agrobacterium (see e.g., Japanese Patent Publication Nos. 7,000/1968, 32,673/1973 and 32,674/1973 and British Patent No. 1,352,938). The curdlan producers Alcalioenes faecalis var. myxogenes NTK-u strain, Aqrobacterium radiobacter U-19 strain are listed respectively under ATCC-21680, ATCC-6466 and ATCC-21679 in the American Type Culture Collection Catalogue of Strains, I, 15th edition, 1982.

Hydrolysates which are low molecular weight derivatives of curdlan may also be used. The method of its production is described in detail in Japanese Patent Application (laid-open) No.83798/1980, or in U.S. Pat. No. 4,454,315.

$\beta$-1,3-glucan may have an average degree of polymerization (DP) below 1000. In particular, its partial hydrolysate with a DP ranging from 6 to about 300 is recommended, and its partial hydrolysate with DP and 15 to about 200 is preferred.

The sulfate of straight chain $\beta$-1,3-glucan for the present invention is an ester resulting from the sulfonation of the hydroxyl group of $\beta$-1,3-glucan or its lower polymers; an ester with an average degree of substitution (DS) of 0.5 to 3 per monosaccharide unit is normally used, and an ester with DS of 1 to 2 is preferably used.

Sulfonation of straight chain $\beta$-1,3-glucan or its low molecular weight polymer can be achieved by the method described in Journal of Biological Chemistry, 239, 2986 (1964). The sulfur content of B-1,3-glucan sulfate is normally over 5% (W/W), preferably about 10 to 21% (W/W), and it is very soluble in water.

Examples of dextran sulfate employable in the present invention include sulfate of dextran, the dextran being produced from sucrose by the action of microorganisms such as *Leuconostoc mesenteroides*.

Dextran sulfate is a partial sulfate of dextran whose principal structure is an alpha (1→≦6) linkage of glucose, and the sulfur content is usually not less than about 12%, preferably about 16 to 20%. The average molecular weight is in the range of from about 1,000 to 40,000,000, preferably in the range of from about 3,000 to 1,000,000 and the dextran sulfate is very soluble in water.

The glucan sulfate employable in the present invention may also be in the form of a salt. As the salt, any pharmaceutically acceptable cation may be employed, e.g., sodium potassium, ammonium, trimethyl ammonium, and the like. The form of glucan sulfate used in the present invention will depend on a number of factors including the ophthalmological agent to be complexed, whether the complexing is by hydrogen binding, covalent binding, interaction with the hydrophobic cavity of cyclodestrin, and the like.

Glucan sulfates may be complexed or otherwise combined with various ophthalmological reagents to provide novel means for delivering and retaining such agents in the ocular tissue. Ophthalmological agents which may be used in combination with glucan sulfate as a vehicle readily may be determined by the skilled artisan by a number of techniques and include: therapeutic agents for the treatment of glaucoma such as epinephrine or its salt, dipivefrin hydrochloride, befunolol hydrochloride, 5-flourouracil (used to prevent glaucoma and after glaucoma surgery to prevent scar formation), pilocarpine and timolol maleate; therapeutic agents for the treatment of cataracts such as pirenoxine; anti-allergic agents such as sodium nomoglicate, cromolyn and amlexanox; anesthetics such as xylocaine, tetracaine and the like; anti-inflammatory agents such as fluorometholone, pranoprofen, hydrocortisone, prednisolone, and other anti-inflammatory steroids as well as non-steroidal antiinflamatory agents such as indomethacin; immune suppressants used to prevent rejection in corneal transplants such as cyclosporin; angiogenic inhibitory agents such as fumagillin and its derivatives such as O-chloracetylcarbamoylfumagillol; antifungal agents such as amphotericin B and nystatin; angiostatic agents such as tetrahydrocortisol, and other angiostatic drugs which may complex or bind with $\beta$-cyclodextrin tetradecasulfate; anti-microbial agents such as ofloxacin, norfloxacin, idoxuridine, erythromycin, neomycin trifluorouridine and acyclovir and the like.

As noted above, diagnostic reagents such as fluorescein may also be used in combination with glucan sulfates in angiograms as discussed in more detail below. Fluorescein has also been recently used in clinical trials in conjunction with laser therapy to treat neovascularization in the cornea, i.e., to reverse neovascularization in corneal transplants and grafts. Laser therapy only works, howvever, when the corneal vessels are enhanced by an intravenous injection of fluorescein before each laser burst, which burst amplifies the laser light inside the blood vessels and closes it off. The problem, however, is that fluorescein alone (without the glucan sulfate of the present invention) is cleared from the blood vessels in less than one minute, and thus, some 50-100 injections of fluoroscein may be required, and which in such large amounts be toxic to the liver. In accordance with the present invention, complexing fluorescein with glucan sulfate increases the retention time of fluorescein in the ocular tissue. In fact, as discussed below, it has been demonstrated that a single injection of fluoroscein when complexed to $\beta$-cyclodextrin tetradecasulfate is retained in the vessels for at least 3 hours, which should greatly reduce the number of injections required for such surgical techniques.

The method of complexing glucan sulfate with an ophthalmological agent will vary in accordance with a number of factors including the glucan sulfate, the ophthalmological agent, the affinity of the agent for the particular glucan sulfate, the ability to form covalent, ionic or hydrogen bonding, or interaction with the hydrophobic cavity of glucan sulfates such as cyclodextrin sulfate.

For example, for cyclodextrin sulfate, the affinity of an ophthalmological agent for the cyclodextrin sulfate and, in particular whether the agent will bind or otherwise be retained in the cavity of the cyclodextrin sulfate can be determined by radioactively labeling the cyclodextrin sulfate, the ophthalmological agent, or both, and precipitating out the complex with e.g., alcohol.

Binding to the surface of the cyclodextrin sulfate can be ascertained by a number of techniques such as competitive inhibition with various indicator dyes.

In certain instances, it may be desirable to covalently bind glucan sulfate and the ophthalmological agent, using conventional techniques.

For complexing of $\beta$-cyclodextrin-cortisone complexes, (see for example Andersen, et al., Arch. Pharm. Chem. Sci. Ed. 11: 61–66 (1983); Armstrong et al., Anal. Chem. 57: 234–237 (1985); and Frank et al., J. Pharm. Sci; Vol 7, No.10: 1215 (1983); the disclosures of which are incorporated by reference herein. See also Folkman et al., Science, 243:1490 (1989), the disclosure of which is incorporated by reference. For complexing of 5-fluorouracil, see Kaji et al., Int. J. Pharm. 24:79 (1985) the disclosure of which is incorporated by reference. For indomethacin complexation with cyclodextrin, see Szejtli et al., Pharmazu 36:694 (1981) the disclosure of which is incorporated by reference.

The amount of glucan sulfate used in combination with any particular ophthalmological agent will depend on a number of factors including the route of administration of the complex, the degree of complexing and strength of the complex formed, as well as the number of doses required per day. In general, the amount will be sufficient to obtain 100% complexing of the guest molecule, i.e., the ophthalmological agent with the glucan sulfate.

EXAMPLE 1

Corneal Penetration of $\beta$-cyclodextrin Tetradecasulfate

A polyethylene ring was glued to the cornea in anesthesized rabbits. Saline containing 1 mg/ml of [S$^{35}$]-$\beta$-cyclodextrin tetradecasulfate was added to each well for up to 120 minutes, after which the wells were removed and the corneas vigorously rinsed with saline. The anterior chamber fluid (ACF) was then aspirated. The corneas were then exised and digested in collegenase and the corneal supernatunt counted.

As can be seen from FIG. 1 [S$^{35}$]-$\beta$-cyclodextrin tetradecasulfate in both the corneas and ACF increased bearly with time, reaching 0.34±0.107µg in the cornea and 0.18±0.014µg in the ACF at two hours.

This experiment also indicates that the label is detected in the ACF and in the corneas up to three hours after the wells containing [S$^{35}$]-$\beta$-cyclodextrin tetradecasulffate have been removed, indicating corneal retention and slow release of $\beta$-cyclodextrin tetradecasulfate into the anterior chamber.

This is in stark contrast to the conventional ocular therapy where ophthalmic agents are removed from the ocular tissue with the exchange of aqueous fluid in the anterior chamber which occurs approximately every thirty minutes.

Example 2

Figure 2:
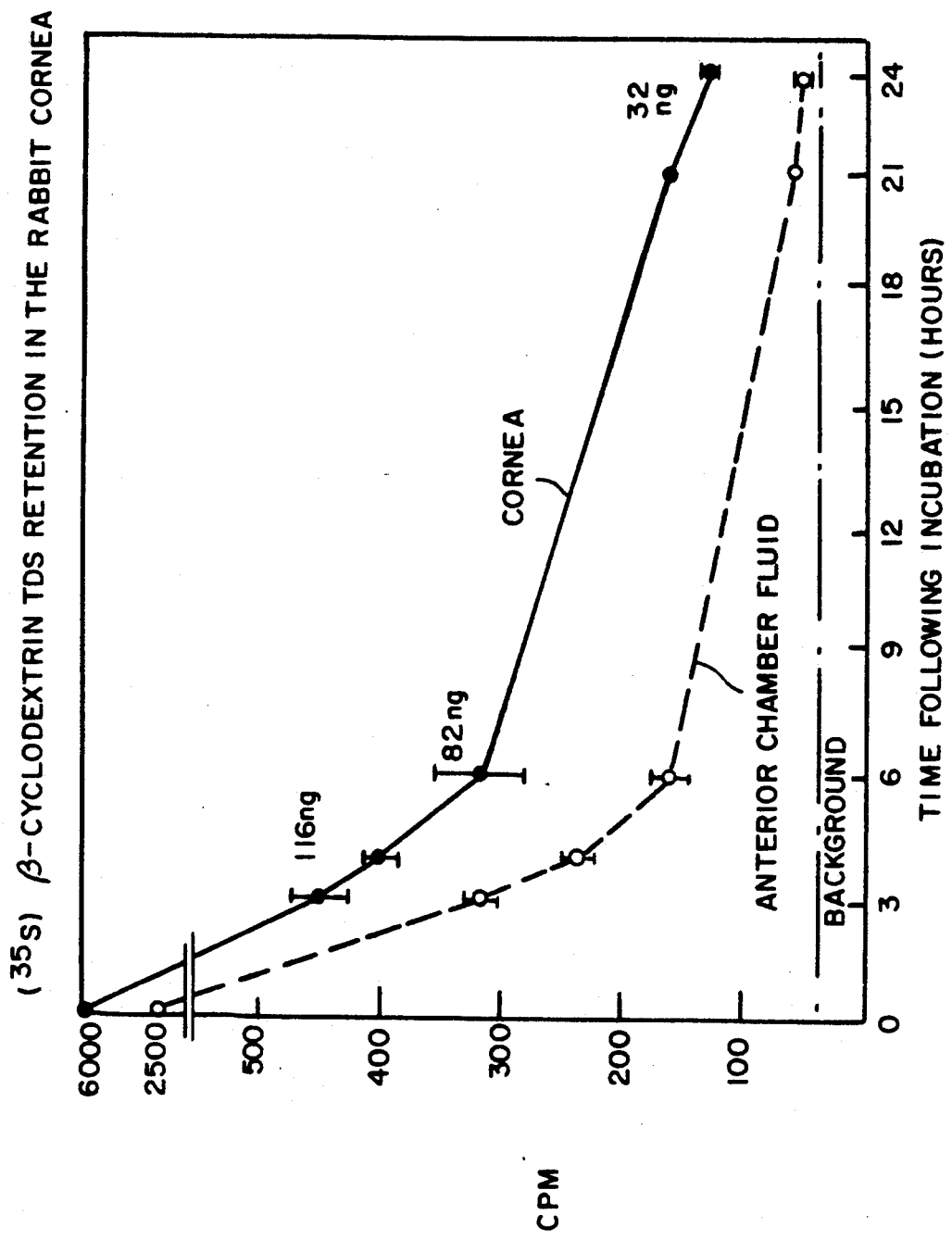
FIG. 2 depicts the retention of radioactively labelled β-cyclodextrin tetradecasulfate in the rabbit cornea over a 24 hour period.

In a similar experiment, it was been demonstrated that after a single application of radioactive $\beta$-cyclodextrin tetradecasulfate, there was a rapid rise in the cornea of labelled $\beta$-cyclodextrin tetradecasulfate and then a gradual fall-off. At the 24 hour mark, however, the cornea still retained three times the concentration of an untreated cornea. As can be seen from FIG. 2, the concentration of $\beta$-cyclodextrin tetradecalsulfate in the aqueous humor parallels that in the cornea, but at lower levels, which is consistent with the slow diffusion which occurs from the corneal depot into the aqueous humor.

EXAMPLE 3

$\beta$-cyclodextrin/Flouroscein Complex $\beta$-cyclodextrin tetradecasulfate was complexed by dissolving both compounds in water with a molar excess of fluoroscein. Specifically, to 6 ml of saline there was added 3 gm of fluoroscein and 30 mgm of $\beta$-cyclodextrin tetradecsulfate (ml saline:gm fluoroscein:-cyclodextrin sulfate of 2:1:10). This yields a molar ratio of flouroscein:cyclodextrin sulfate of about 600:1. This produced a light green solution which was placed shaken at 37° C. rotator shaking plate for 4 days. Ethanol was then added (100%) at 1:5 v/v followed by centrifugation at about 2000 g for about 20 minutes. A green precipitate formed. The pellet was repeatedly washed with ethanol (100%) until the supernatant was colorless (until the ethanolic solution was clear and contained no fluorscein by UV fluorescence), and then by vacuum dried.

Example 4

The water soluble complex described in Example 3 was injected into the carotid artery of rabbits who had neovascularization in the cornea induced by a pellet of endotoxin implanted one week earlier. After a single injection, the new vessels in the cornea were still flourescing green 3 hours later.

Similarly, when the cyclodextrin-fluorscein complex, dissolved in an aqueous solution of methylcellulose (0.45%), was applied to the rabbit cornea, Descemet's membrane in the cornea also glowed green more than 3 hours later when histological sections of the corneas were examined. Flouroscein alone disappeared from the corneal vessels within a few minutes after being injected into the carotid artery, and was not found in Descemet's membrane.

What is claimed is:

1. A method for increasing retention of an opthalmological agent for an ocular tissue comprising complexing an ophthalmological agent with a glucan sulfate and administering the complex to said ocular tissue, wherein the glucan sulfate is selected from the group consisting of dextran sulfate, cyclodextrin sulfate or $\beta$-1,3-glucan sulfate.

2. The method of claim 1, wherein the glucan sulfate is cyclodextrin.

3. The method of claim 2, wherein the cyclodextrin sulfate has a sulfur content of greater than about 3%(w/w).

4. The method of claim 3, wherein the cyclodextrin sulfate has a sulfur content of between about 12 and 24%(w/w).

5. The method of claim 4, wherein the cyclodextrin sulfate has a sulfur content between about 15 and 21%(w/w).

6. The method of claim 2, wherein the cyclodextrin sulfate is selected from the group consisting of alpha-, beta- or gamma-cyclodextrin sulfate.

7. The method of claim 2, wherein the cyclodextrin sulfate is $\beta$-cyclodextrin tetradecasulfate.

8. The method of claim 1, wherein the glucan sulfate is β-1,3-glucan sulfate.

9. The method of claim 8, wherein the β-1,3-glucan sulfate has a sulfur content greater than about 5%(w/w).

10. The method of claim 9, wherein the β-1,3-glucan sulfate has a sulfur content between about 10 to 21% (w/w).

11. The method of claim 8, wherein the β-1,3-glucan sulfate is a partial hydrolysate having an average degree of polymerization below about 1000.

12. The method of claim 12, wherein the average degree of polymerization is between 6 and about 300.

13. The method of claim 11, wherein the degree of polymerization is between about 45 and 200.

14. The method of claim 1, where in the glucan sulfate is dextran sulfate.

15. The method of claim 14, wherein the dextran sulfate has a sulfur content greater than about 12%(w/w).

16. The method of claim 15, wherein the sulfur content of the dextran sulfate is between about 15 and 21%(w/w).

17. The method of claim 14, wherein the average molecular weight of the dextran sulfate is between about 1000 and 40,000,000.

18. The method of claim 16, wherein the average molecular weight of the dextran sulfate is between about 3,000 and 1,000,000.

19. The method of claim 1, wherein the complex is administered topically.

20. The method of claim 1, wherein the ophthalmological agent is administered topically and the glucan sulfate is administered topically and the complex forms in vivo.

21. The method of claim 1, wherein the complex is administered parentally.

22. The method of claim 1, wherein the ophthalmological agent is administered parentally and the glucan sulfate is administered parentally and the complex is formed in vivo.

23. The method of claim 1, wherein the ophthalmological agent comprises a therapeutic agent for the treatment of glaucoma; a therapeutic agent for the treatment of cataracts; an anti-allergic agent; and anesthetic; and anti-inflammatory agent; an immune suppressant; an angiogenic inhibitory agent; an antifungal agent; an angiostatic agent; a diagnostic agent, or an antimicrobial agent.

24. The method of claim 23, wherein the opthalmological agent comprises epinephrine, dipivefrin hydrochloride, befunolol hydrochloride, 5-O-Flourouracil, pilocarpine, timolol maleate, pirenoxine, sodium monoglicate, cromolyn, amlexanox, xylocaine, tetracaine, florometholone, pranoprofn, prednisolone, indomethacin, cyclosporin, amphotericin B, nystatin, tetrahydrocortisol, ofloxacin, norfloxacin, idoxuridine, erythromybin, neomycin, trifluororidine, acyclovir, flourescein or pharmaceutically acceptable salts thereof.

25. The method of claim 1, wherein the ophthalmological agent is hydrocortisone.

26. The method of claim 1, wherein the ophthalmological agent is fumagillin.

27. The method of claim 1, wherein the ophthalmological agent is O-chloracetylcarbamoylfumagillol.

* * * * *

UNITED STATES PATENT AND TRADEMARK OFFICE
CERTIFICATE OF CORRECTION

PATENT NO. : 5,227,372

DATED : July 13, 1993

INVENTOR(S) : Judah M. Folkman

It is certified that error appears in the above-indentified patent and that said Letters Patent is hereby corrected as shown below:

Cover page of patent, on the right hand side of the figure, replace "($^{35}$S) -CYCLODEXTRIN(ng)" with --($^{35}$S) $\beta$-CYCLODEXTRIN(ng)--.

Column 3, line 47, replace "vesels" with --vessels--.

Column 4, line 59, replace "respectively" with --respectively).--.

Column 5, line 11, replace "Alcaligenus" with --*Alcaligenes*--.

Column 5, line 12, replace "water-soluble" with --water-insoluble--.

Column 5, line 19, replace "(1->3)" with --(1→3)--.

Column 5, line 20, replace "produce" with --produced--.

Column 6, line 5, replace "cyclodestrin" with --cyclodextrin--.

Column 6, line 15, replace "5-flourouracil" with --5-fluorouracil--.

Column 6, line 24, replace "antiinflammatory" with --anti-inflammatory--.

Column 6, line 28, replace "O-chloracetylcarbamoylfumagillol" with --O-chloroacetylacarbamoylfumagillol--.

Column 6, line 43, replace "howvever" with --however--.

Column 7, line 45, replace "collegenase" with --collagenase--.

UNITED STATES PATENT AND TRADEMARK OFFICE
CERTIFICATE OF CORRECTION

PATENT NO. : 5,227,372

DATED : July 13, 1993

INVENTOR(S) : Judah M. Folkman

It is certified that error appears in the above-indentified patent and that said Letters Patent is hereby corrected as shown below:

Column 7, line 46, replace "supernatunt" with --supernatant--.

Column 7, line 54, replace "tetradecasulffate" with --tetradecasulfate--.

Column 8, line 9, replace "Flouroscein" with --Fluorescein--.

Column 8, line 14, replace "tetradecasulfate" with --tetradecasulfate--.

Column 8, line 16, replace "fluorscein:cyclodextrin" with --fluoroscein:cyclodextrin--.

Column 8, line 35, replace "cyclodextrin-" with --cyclodextran- --.

Column 8, line 35, replace "fluorscein" with --fluorescein--.

Column 8, line 40, replace "Flouroscein" with --Fluorescein--.

Column 9, line 16, replace "where in" with --wherein--.

Column 10, line 19, replace "5-O-Flourouracil" with --5-O-Fluorouracil--.

Column 10, line 32, replace "O-chloracetyl-" with --O-chloroacetyl- --.

UNITED STATES PATENT AND TRADEMARK OFFICE
CERTIFICATE OF CORRECTION

PATENT NO.   : 5,227,372
DATED        : July 13, 1993
INVENTOR(S)  : Judah M. Folkman It is certified that error appears in the above-indentified patent and that said Letters Patent is hereby corrected as shown below:

Column 3, line 44, replace "the its" with --the cornea, its--.

Column 3, line 45, replace ", he iris" with --the iris--.

Column 5, line 11, replace "Aorobacterium" with --*Agrobacterium*--.

Column 5, line 21, replace "Alcalioenes" with --*Alcaligenes*--.

Column 5, line 21, replace "Agrobacterium" with --*Agrobacterium*--.

Column 5, line 24, replace "Alcalioenes faecalis" with --*Alcaligenes faecalis*--.

Column 5, line 24, replace "myxogenes" with --*myxogenes*--.

Column 5, line 25, replace "Aqrobacterium" with --*Agrobacterium*--.

Column 5, line 25, replace "radiobacter" with --*radiobacter*--.

Column 5, line 49, replace "239" with --*239*--.

Column 5, line 49, replace "B-1,3-glucan" with --$\beta$-1,3-glucan--.

Column 5, line 57, replace "(1→ $\leq$6)" with --(1→6)--.

UNITED STATES PATENT AND TRADEMARK OFFICE
CERTIFICATE OF CORRECTION

PATENT NO. : 5,227,372
DATED : July 13, 1993
INVENTOR(S) : Judah M. Folkman

It is certified that error appears in the above-indentified patent and that said Letters Patent is hereby corrected as shown below:

Column 8, line 46, replace "agent for" with --agent at--.

Column 8, line 53, replace "cyclodextrin" with --cyclodextrin sulfate--.

Column 9, line 12, replace "of claim 12," with --of claim 11,--.

Column 9, line 14, replace "of claim 11," with --of claim 12,--.

Column 9, line 15, replace "about 45" with --15 and about--.

UNITED STATES PATENT AND TRADEMARK OFFICE
CERTIFICATE OF CORRECTION

PATENT NO. : 5,227,372
DATED : July 13, 1993
INVENTOR(S) : Judah M. Folkman

It is certified that error appears in the above-indentified patent and that said Letters Patent is hereby corrected as shown below:

Column 10, line 6, replace "parentally" with --parenterally--.

Column 10, line 7, replace "parentally" with --parenterally--.

Column 10, line 8, replace "in vivo" with --*in vivo*--.

Column 10, line 22, replace "pranoprofn" with --pranoprofen--.

Column 10, line 25, replace "erythromybin" with --erythromycin--.

Signed and Sealed this

Twenty-seventh Day of September, 1994

Attest:

BRUCE LEHMAN

Attesting Officer  Commissioner of Patents and Trademarks